United States Patent
Mackin

(10) Patent No.: US 10,272,166 B2
(45) Date of Patent: Apr. 30, 2019

(54) SYSTEMS AND METHODS FOR SANITIZING A TRAY TABLE

(71) Applicant: THE BOEING COMPANY, Chicago, IL (US)

(72) Inventor: Steven George Mackin, Seattle, WA (US)

(73) Assignee: The Boeing Company, Chicago, IL (US)

( * ) Notice: Subject to any disclaimer, the term of this patent is extended or adjusted under 35 U.S.C. 154(b) by 88 days.

(21) Appl. No.: 15/497,352

(22) Filed: Apr. 26, 2017

(65) Prior Publication Data

US 2017/0224854 A1 Aug. 10, 2017

Related U.S. Application Data

(62) Division of application No. 14/633,374, filed on Feb. 27, 2015, now Pat. No. 9,662,410.

(51) Int. Cl.
| | | |
|---|---|---|
| *A61L 2/10* | (2006.01) | |
| *A61L 2/24* | (2006.01) | |
| *B60N 3/00* | (2006.01) | |
| *B64D 11/06* | (2006.01) | |

(52) U.S. Cl.
CPC .................. *A61L 2/10* (2013.01); *A61L 2/24* (2013.01); *B60N 3/004* (2013.01); *B64D 11/06* (2013.01); *B64D 11/0638* (2014.12); *A61L 2202/11* (2013.01); *A61L 2202/14* (2013.01)

(58) Field of Classification Search
CPC ............................... A61L 2/10; A61L 2202/11
See application file for complete search history.

(56) References Cited

U.S. PATENT DOCUMENTS

| | | |
|---|---|---|
| 2003/0030015 A1 | 2/2003 | Waluszko |
| 2005/0212239 A1 | 9/2005 | Carter |
| 2008/0067417 A1 | 3/2008 | Lane |
| 2012/0313532 A1 | 12/2012 | Stibich |
| 2013/0062534 A1 | 3/2013 | Cole |
| 2014/0059796 A1 | 3/2014 | Boodaghians |
| 2014/0241941 A1 | 8/2014 | Kreitendberg |
| 2015/0090904 A1 | 4/2015 | Cole |
| 2016/0000951 A1 | 1/2016 | Kreiner |

FOREIGN PATENT DOCUMENTS

| | | |
|---|---|---|
| CN | 102429467 A | 5/2012 |
| CN | 202820389 U | 3/2013 |
| CN | 103445536 A | 12/2013 |
| DE | 102012006972 | 10/2013 |
| EP | 2772272 | 9/2014 |
| JP | 11196847 A | 7/1999 |
| WO | WO 2014075040 | 5/2014 |

OTHER PUBLICATIONS

Extended EP Search Report for EP 16155002.5-1370, dated Apr. 29, 2016.

*Primary Examiner* — Kevin Joyner
(74) *Attorney, Agent, or Firm* — Joseph M. Butscher; The Small Patent Law Group LLC

(57) ABSTRACT

A system for sanitizing a tray table may include a sanitation assembly operatively coupled to the tray table. The sanitation assembly includes an ultraviolet (UV) light source configured to emit UV light, and a sanitation control unit operatively coupled to the UV light source. The sanitation control unit operates the UV light source to emit the UV light onto the tray table when the tray table is secured in an upright position, and prevents the UV light source from emitting the UV light when the tray table is not secured in the upright position.

25 Claims, 10 Drawing Sheets

SYSTEMS AND METHODS FOR SANITIZING A TRAY TABLE

RELATED APPLICATIONS

This application is a division of U.S. patent application Ser. No. 14/633,374, entitled "Systems and Methods for Sanitizing a Tray Table," filed Feb. 27, 2015, now U.S. Pat. No. 9,662,410, which is hereby incorporated by reference in its entirety.

FIELD OF EMBODIMENTS OF THE DISCLOSURE

Embodiments of the present disclosure generally relate to systems and methods for sanitizing a tray table, such as may be moveably secured to a back of a seat within a vehicle.

BACKGROUND OF THE DISCLOSURE

Commercial aircraft include an interior cabin that may be divided into numerous sections. A cockpit is generally separated from a passenger cabin, which may include a first class section, a business class section, and a coach section. The passenger cabin may also include one or more work areas for flight personnel, such as galleys, which may include food and beverage storage structures. One or more aisles pass through the passenger cabin and connect each of the passenger sections to one or more paths to one or more doors of the aircraft.

Seat assemblies are secured within the cabin. Each seat assembly may include a tray table secured to a back portion. The tray table is configured to be moved between a stowed, upright position, and a supporting position. During a flight, for example, an individual seated behind a particular seat assembly may move the tray table to the supporting position in order to support objects thereon. For example, during in-flight beverage service, the tray table may be moved to the supporting position so that a passenger may place a beverage and snacks on a supporting surface of the tray table. During take-off and landing phases of flight, the tray tables are secured in the stowed, upright position.

As can be appreciated, during a typical flight, the tray tables may become contaminated. For example, a passenger may spill a beverage on a tray table. Further, the tray table may become covered with crumbs. Also, a passenger may sneeze in proximity to the tray table, such that germs are spread onto the supporting surface. In short, a tray table may be covered with various contaminants, such as food and beverage remnants, germs, bacteria, and the like.

Accordingly, tray tables are periodically cleaned by flight attendants or ground-based cleaning personnel between flights. However, there may not be sufficient time to effectively clean each tray table. Moreover, individual flight attendants may not thoroughly clean each tray table. As such, various contaminants may remain on particular tray tables, which may pose real and/or perceived health concerns to future passengers.

Accordingly, a need exists for a system and method for effectively and efficiently sanitizing tray tables within a vehicle.

SUMMARY OF THE DISCLOSURE

Certain embodiments of the present disclosure provide a system for sanitizing a tray table. The system may include a sanitation assembly operatively coupled to the tray table. The sanitation assembly may include an ultraviolet (UV) light source configured to emit UV light, and a sanitation control unit operatively coupled to the UV light source. The sanitation control unit may be configured to operate the UV light source to emit the UV light onto the tray table when the tray table is secured in an upright position, and prevents the UV light source from emitting the UV light when the tray table is not secured in the upright position.

The system may also include a tray table position sensor in communication with the sanitation control unit. The tray table position sensor may be configured to detect when the tray table is secured in the upright position.

In at least one embodiment, the sanitation assembly is securely connected to a seat assembly. For example, the sanitation assembly may be secured to a back portion of a backrest of the seat assembly.

The UV light source may be configured to emit UV germicidal irradiation. The UV light source may include one or more of a low pressure mercury discharge lamp, one or more fiber optic couplings, or one or more light emitting diodes, for example.

The system may also include a passenger interface in communication with the sanitation control unit. The passenger interface may be configured to allow a passenger to activate a sanitation cycle when the tray table is secured in the upright position.

The system may also include a master control unit remotely located from and in communication with the sanitation control unit. The master control unit may be configured to monitor and control operation of the sanitation assembly for the tray table and those of other tray tables.

In at least one embodiment, one or both of the sanitation assembly and/or the tray table includes one or more reflective surfaces that are configured to reflect the UV light emitted from the UV light source onto surfaces of the tray table. A covering filter may be secured to outer surfaces of one of the sanitation assembly or the tray table. The covering filter is configured to filter the UV light so that UV radiation is not emitted outside of the tray table.

The sanitation assembly may also include a shutter moveably secured over the UV light source. The shutter may be in a closed position that covers the UV light source when the tray table is not secured in the upright position. The shutter may be moved to an open position that exposes the UV light source when the tray table is secured in the upright position.

Certain embodiments of the present disclosure provide a method of sanitizing a tray table. The method may include emitting ultraviolet (UV) light from a UV light source onto the tray table when the tray table is secured in an upright position, and preventing emission of the UV light from the UV light source when the tray table is not secured in the upright position.

Certain embodiments of the present disclosure provide a vehicle that includes an internal cabin, and a plurality of seat assemblies within the internal cabin. Each of the plurality of seat assemblies may include a tray table and a sanitation assembly operatively coupled to the tray table. Each sanitation assembly may include an ultraviolet (UV) light source configured to emit UV light, and a sanitation control unit operatively coupled to the UV light source. The sanitation control unit operates the UV light source to emit the UV light onto the tray table when the tray table is secured in an upright position. The sanitation control unit prevents the UV light source from emitting the UV light when the tray table is not secured in the upright position.

The vehicle may also include a master control unit remotely located from and in communication with the sanitation control units of the plurality of seat assemblies. The master control unit is configured to monitor operation of the sanitation assemblies of the plurality of seat assemblies. The master control unit may be configured to monitor power consumption within the vehicle and selectively activate and deactivate sanitation cycles for the tray tables of the plurality of seat assemblies based on a comparison of the power consumption and one or more power thresholds.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Embodiments of the present disclosure provide systems and methods for automatically sanitizing a tray table within a vehicle, such as a commercial aircraft. The systems and methods may include using at least one ultraviolet (UV) light source to generate UV germicidal irradiation that sanitizes the tray table. In at least one embodiment, when the tray table is secured in a stowed, upright position, the UV light source may be activated. A passenger and/or crew member may initiate a sanitation cycle when one or more tray tables are secured in the stowed, upright position. When a tray table is in a supporting position, the UV light source is deactivated and may be covered.

Embodiments of the present disclosure allow for efficient and effective tray table sanitation. Each passenger may be able to activate a sanitation cycle when a tray table is in the stowed, upright position. Optionally, one or more crew members of a vehicle, such as flight attendants, may activate a sanitation cycle for multiple stowed tray tables.

Figure 1:
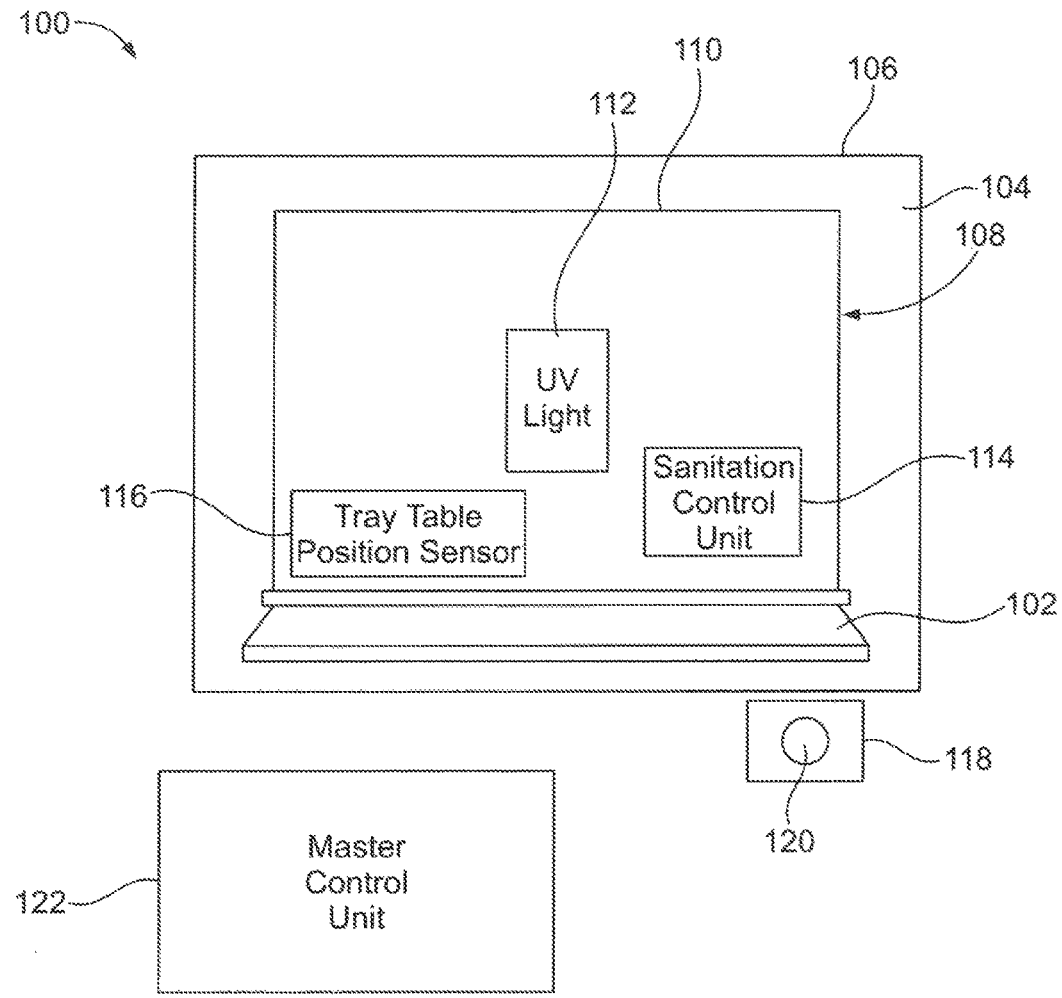
FIG. 1 illustrates a schematic block diagram of a system for sanitizing a tray table, according to an embodiment of the present disclosure.

FIG. 1 illustrates a schematic block diagram of a system 100 for sanitizing a tray table 102, according to an embodiment of the present disclosure. The tray table 102 is moveably secured to a back 104 of a seat assembly 106. For example, the tray table 102 may be pivotally secured to the back 104 of the seat assembly 106 through lateral arms that are configured to be pivoted between a stowed, upright position, and a supporting position, in which the tray table 102 is generally parallel to a floor within a cabin of a vehicle.

The seat assembly 106 may also include a sanitizing assembly 108 that is configured to automatically sanitize the tray table 102 when the tray table 102 is secured in the stowed, upright position. When the tray table 102 is not secured in the upright position, the sanitizing assembly 108 refrains from sanitizing the tray table 102. The sanitizing assembly 108 may be securely mounted on and/or in the back 104 of the seat assembly 106, for example.

The sanitizing assembly 108 may include a housing 110 that securely retains an ultraviolet (UV) light source 112 operatively connected to a sanitation control unit 114. The sanitation control unit 114 may be a sanitation control circuit that includes one or more processors (such as microprocessors, microcontrollers, etc.), one or more memories, and/or the like that are configured to control operation of the sanitation assembly 106. In short, the sanitation control unit 114 may be or include a central processing unit (CPU) that may be or include any computing device, memory, module, component, or the like that is configured to control operation of the sanitizing assembly 108.

The UV light source 112 may be or include a low pressure mercury vapor discharge lamp, for example. For example, the UV light source 112 may include a 9 W germicidal UV lamp. Alternatively, the UV light source 112 may include one or more light-emitting diodes (LEDs) that are configured to emit ultraviolet light. As another alternative, the UV light source 112 may be remotely located from the housing 110 (such as within a base of the seat assembly 106), and connected to light outputs of the housing 110 through fiber optic couplings.

UV germicidal irradiation uses UV light at one or more wavelengths to kill microorganisms. For example, the UV light source 112 may emit short-wavelength UV radiation that destroys nucleic acids in various microorganisms, leaving them unable to perform cellular functions. In general, the UV light source 112 is configured to emit UV light that kills microorganisms, including pathogens, viruses, germs, bacteria, and molds, for example.

A tray table position sensor 116 may be in communication with the sanitation control unit 114 and configured to detect when the tray table 102 is secured in the stowed, upright position. The tray table position sensor 116 may be or include one or more components configured to detect a position of the tray table 102. For example, the tray table position sensor 116 may include one or more of a Hall effect sensor, an infrared or laser assembly configured to detect if the tray table 102 breaks a particular plane defined by a light beam, and/or the like. As shown, the tray table position sensor 116 may be secured within the housing 110. Alternatively, the tray table position sensor 116 may be remotely located from the housing 110, such within the seat assembly 106 at a position above, below, or to one or both sides of the housing 110.

A passenger interface 118 (such as a touchscreen display) may be in communication with the sanitation control unit 114. The passenger interface 118 may include a button 120 (such as a mechanical button or digital representation of a button on a touchscreen display) that may be engaged by a passenger seated in a seat assembly behind the seat assembly 106 so that the sanitizing assembly 108 may sanitize the tray table 102 when secured in the upright position. The passenger interface 118 may be operatively connected to the sanitation control unit 114 through a wired or wireless connection. In at least one embodiment, the passenger interface 118 may be secured to the back 104 of the seat assembly 106. In at least one other embodiment, the passenger interface 118 may be secured to a portion of another seat assembly behind the seat assembly 106. For example, the passenger interface 118 may be secured within an armrest of a seat assembly. In at least one embodiment, the system 100 may not include the passenger interface 118.

The system 100 may also include a master control unit 122, which may include one or more processors (such as microprocessors, microcontrollers, etc.), one or more memories, and/or the like. The master control unit 122 may be or include a central processing unit (CPU) that may be or include any computing device, memory, module, component, or the like. The master control unit 122 may be remotely located from the seat assembly 106, such as within a vehicle crew workstation (for example, within a galley area between seating sections of the vehicle). The master control unit 122 may be in communication with the sanitation control unit 114 of the seat assembly 106 and other sanitation control units of other seat assemblies through wired or wireless connections. The master control unit 122 may be configured to monitor operation of each sanitizing assembly 108 (such as whether it is activated or deactivated) and control operation of multiple sanitizing assemblies 108, such as by sequentially activating one or more sanitizing assemblies at particular times.

In operation, when the tray table 102 is not secured in the upright position, the sanitation control unit 114 prohibits the UV light source 112 from emitting light energy. The sanitation control unit 114 detects whether or not the tray table 102 is secured in the upright position through signals received from the tray table position sensor 116. In response to the sanitation control unit 114 detecting that the tray table 102 is securely stowed in the upright position, such as through signals detected by the tray table position sensor 116, the sanitation control unit 114 may transition to a standby mode, in which a sanitation cycle may be activated.

The sanitation cycle may be activated in response to a passenger engaging the button 120 of the passenger interface 118. The sanitation cycle may also be activated in response to an individual (for example, a crew member) engaging an interface of the master control unit 122. Alternatively, the system 100 may not include the passenger interface 118 or the master control unit 122. In at least one embodiment, the sanitation control unit 114 may automatically activate the sanitation cycle in response to the tray table 102 being secured in the stowed, upright position. Further, in at least one embodiment, the sanitation control unit 114 may automatically activate the sanitation cycle in response to all passengers deplaning.

The sanitation cycle may be controlled by instructions stored in memory of the sanitation control unit 114 and/or the master control unit 122. For example, if the UV light source 112 includes one or more 9 W UV lamps, the sanitation cycle may last five to ten minutes. In another embodiment, the UV light source 112 may include a 500 W UV lamp, in which case the sanitation cycle may last 1 millisecond or less. After completion of the sanitation cycle, the sanitation control unit 114 deactivates the UV light source 112. The 9 W and 500 W UV lamps are merely examples. It is to be understood that the wattage of the UV lamps may be less than 9 W or even greater than 500 W, and wattages therebetween. Further, the cycle times noted above are merely examples. The sanitation cycle may be greater or lesser than 1 millisecond, or greater or lesser than five or ten minutes. It has been found that with increased wattage of the UV light source, the time of the sanitation cycle decreases. Also, in at least one embodiment, the UV light source 112 may include a high wattage (for example, greater than 200 W) bulb that flashes in less than a second to sanitize a tray table surface. In such an embodiment, a control interface may provide an option for flash sanitation.

The UV light emitted by the UV light source 112 during the sanitation cycle sanitizes the tray table 102. For example, the UV light kills germs, bacteria, pathogens, and the like that may be present on the tray table 102 during the sanitation cycle. As such, after the sanitation cycle is complete, when the tray table 102 is moved to the supporting position, the tray table 102 is free of germs, bacteria, pathogens, and the like.

The master control unit 122 may be used to monitor power consumption within a vehicle for example, and operate multiple sanitation assemblies accordingly. For example, the master control unit 122 may activate sanitation cycles for all sanitation assemblies when all of the tray tables are secured in upright positions, if the total power consumption of the sanitation assemblies does not exceed a predefined threshold. Optionally, the master control unit 122 may activate sanitation cycles for subsets or groups of sanitation assemblies in order to control power consumption. After a first group or subset of sanitation assemblies have completed a sanitation cycle, the master control unit 122 may deactivate those sanitation assemblies and activate another group or subset of sanitation assemblies. In this manner, the master control unit 122 may sequentially activate and deactivate groups of sanitation assemblies within a vehicle.

Figure 2:
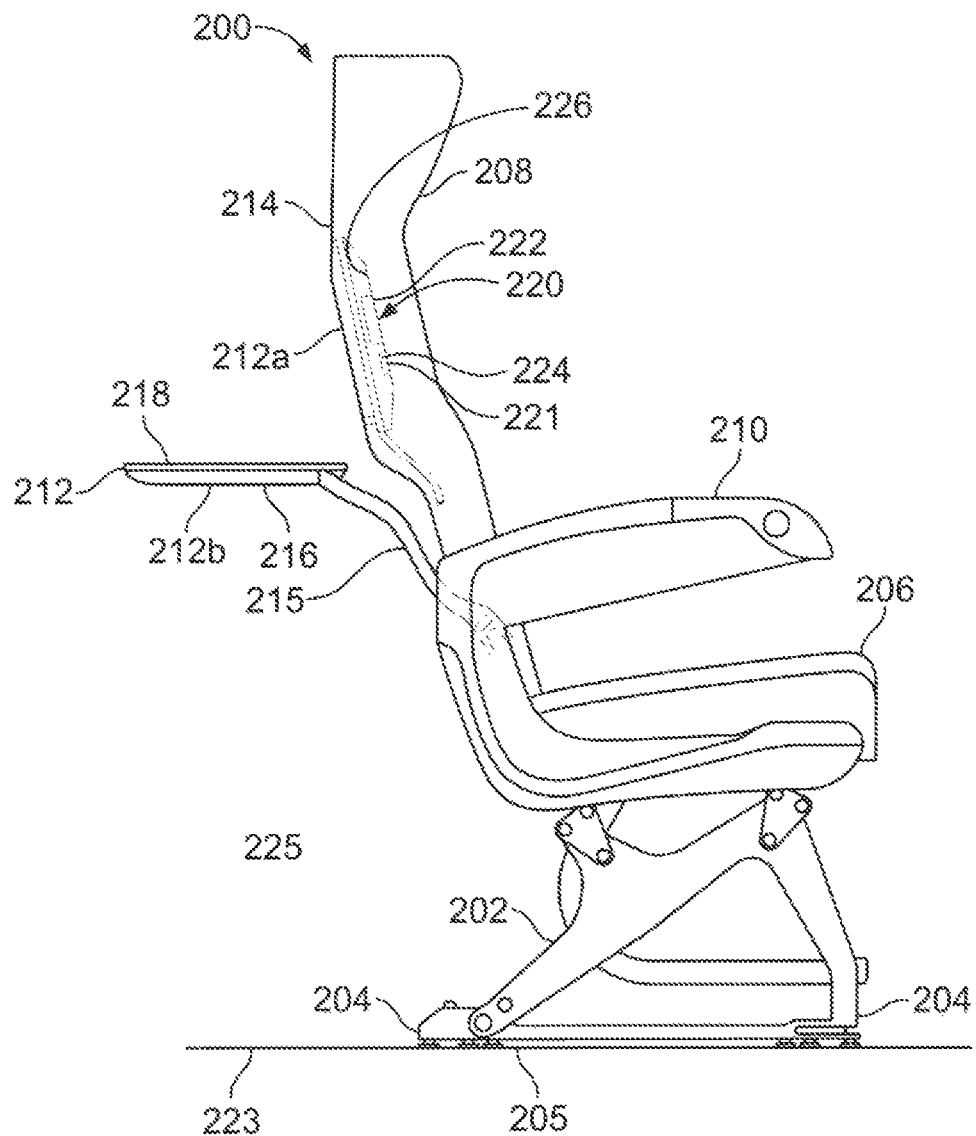
FIG. 2 is a diagrammatic representation of a side view of a seat assembly, according to an embodiment of the present disclosure.

FIG. 2 is a diagrammatic representation of a side view of a seat assembly 200, according to an embodiment of the present disclosure. The seat assembly 200 may be configured to be secured within a cabin of a vehicle, such as a commercial aircraft.

The seat assembly 200 includes a base 202 having legs 204 that may be secured to tracks 205 within a cabin of a vehicle. The legs 204 may include fittings, fasteners, or the like that are configured to securely connect the legs 204 to the tracks 206. The base 202 supports a seat cushion 206 and a backrest 208. Arm rests 210 may be pivotally secured to the backrest 208.

A tray table 212 is moveably secured to a back 214 of the backrest 208 through lateral arms 215 that are pivotally secured to the back 214. The tray table 212 is configured to be moved between a stowed, upright position 212a and a supporting position 212b. In the upright position 212a, the tray table 212 is securely locked in place such that an underside 216 may be flush with the back 214, and a supporting surface 218 abuts against a sanitation assembly 220 secured to or within the backrest 208. The sanitation assembly 220 may be an example of the sanitation assembly 108 shown and described with respect to FIG. 1. For example, the sanitation assembly 220 may be contained within a housing 221 and may include a UV light source 222 operatively connected to a sanitation control unit 224.

The housing 221 may include a reflective wall 226 that is configured to reflect UV light emitted from the UV light source 222 onto the supporting surface 218 when the tray table 212 is in the upright position 212a. Additionally, the supporting surface 218 may be or include a reflective surface that is configured to reflect light emitted by the UV light source 222. The reflective surfaces may be or include surfaces formed of or including aluminum, stainless steel, mirrors, and/or the like. In at least one embodiment, the supporting surface 218 may include a reflective surface covered by a transparent covering layer, such as Plexiglas, clear plastic, or the like.

In the supporting position 212b, the supporting surface 218 may be exposed and substantially parallel to a floor 223 of the cabin 225. As such, a passenger may rest objects, such as cups, cans, or the like, on the supporting surface 218 in the supporting position 212b.

Figure 3:
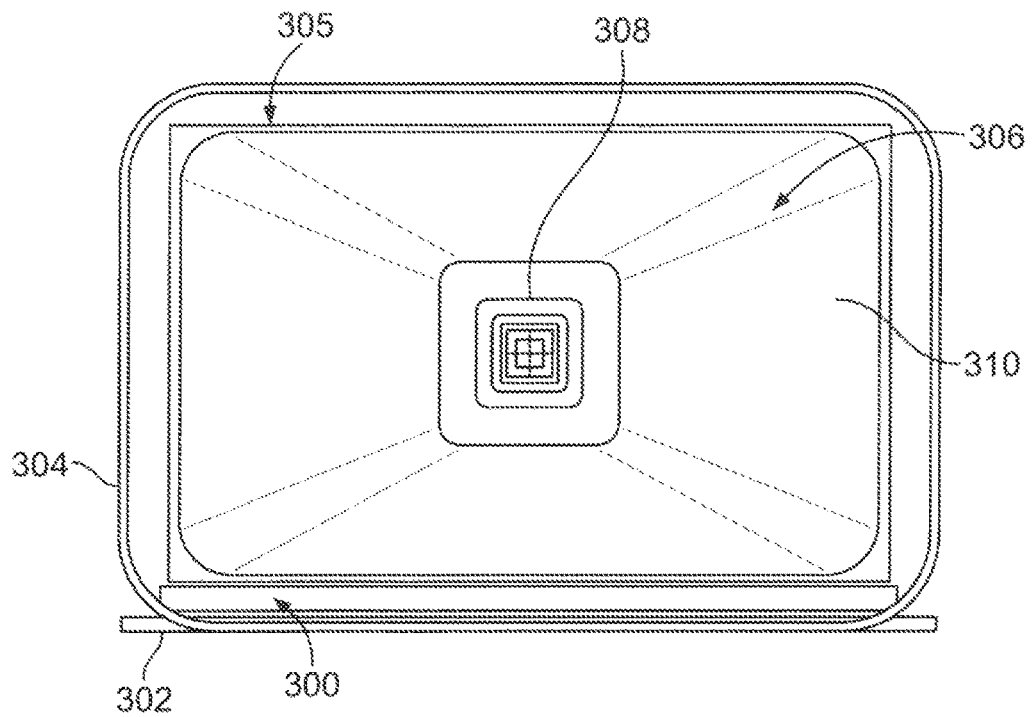
FIG. 3 is a diagrammatic representation of a front view of a tray table in a supporting position, according to an embodiment of the present disclosure.
Figure 4:
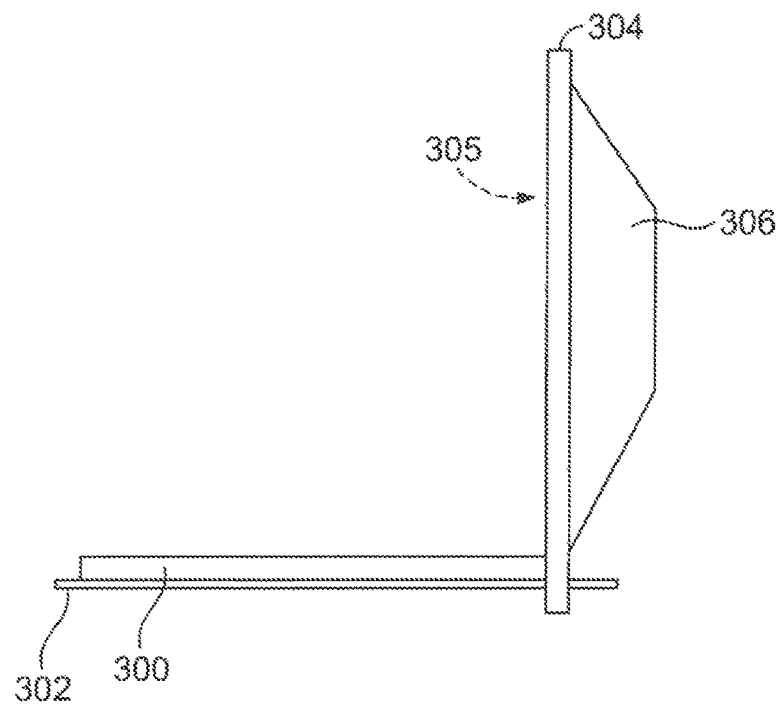
FIG. 4 is a diagrammatic representation of a side view of a tray table in a supporting position, according to an embodiment of the present disclosure.

FIG. 3 is a diagrammatic representation of a front view of a tray table 300 in a supporting position, according to an embodiment of the present disclosure. FIG. 4 is a diagrammatic representation of a side view of the tray table 300 in the supporting position. Referring to FIGS. 3 and 4, a covering filter 302 may be secured to an underside of the tray table 300. The covering filter 302 is configured to abut against an outer edge of a reflective rim 304 that is secured around a light-emitting outlet 305 of a sanitation assembly 306 (such as any of those described in the present application), which includes a UV light source 308. A covering layer 310, such as glass, Plexiglas, clear plastic, or the like, may cover the UV light source 308 so that a passenger may not touch the UV light source 308. The covering layer 310 may hide the UV light source 308 when the tray table 300 is in the supporting position. For example, the covering layer 310 may be a one way mirror that hides the UV light source 308, but allows UV light to pass therethrough when the tray table 300 is secured in an upright position.

The reflective rim 304 may be formed of a reflective material, such as any of those described above. Additionally, surfaces of the sanitation assembly 306 surrounding the UV light source 308 may also be formed of and/or covered with a reflective material.

When the tray table is secured in the upright position, the covering filter 302 abuts against the reflective rim 304 and is configured to filter UV light emitted from the UV light source 308. Thus, when the UV light source 308 is active, the covering filter 302 blocks UV radiation from passing therethrough, but allows passage of other light that is safe for viewing by individuals. As such, during operation, the covering filter may produce a filtered light ring (for example, a peripheral glow) around the sanitation assembly 306 that is visible to individuals. Generation of the light ring indicates to individuals that the sanitation assembly 306 is operating to sanitize the tray table 300. Alternatively, instead of a light ring, the covering filter 302 may allow for filtered light to be emitted (e.g., glow) at distinct areas other than a ring. For example, the covering filter 302 may allow for filtered light to be emitted from a point on the sanitation assembly 306.

As shown, the reflective rim 304 may be an outwardly extending rim that is secured around a portion of the sanitation assembly 306. Alternatively, the reflective rim 304 may be fixed around the tray table 300, for example.

Figure 5:
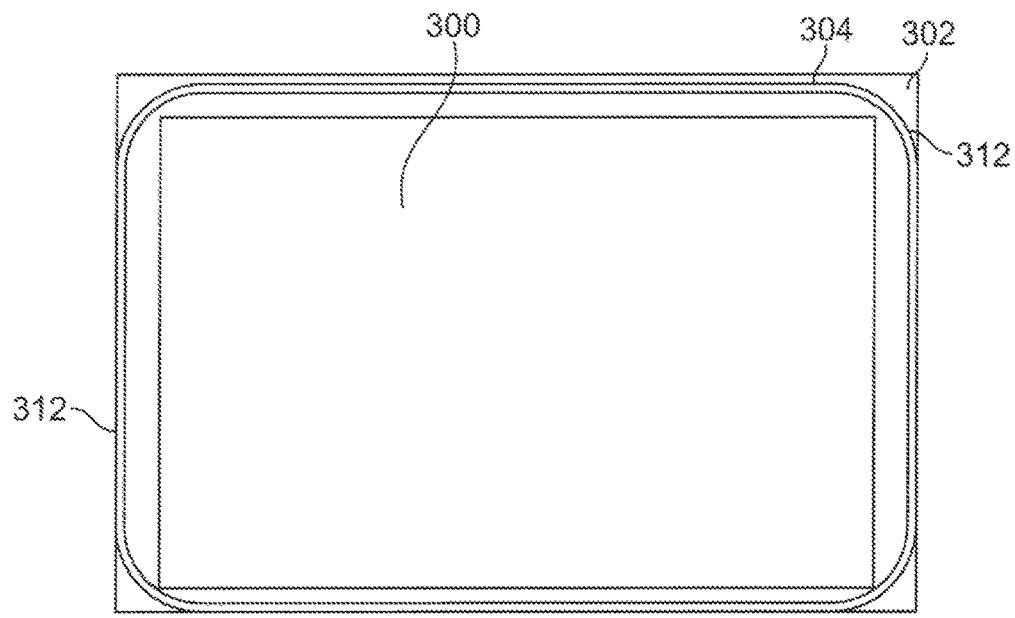
FIG. 5 is a diagrammatic representation of a front view of a tray table in a secured upright position, according to an embodiment of the present disclosure.
Figure 6:
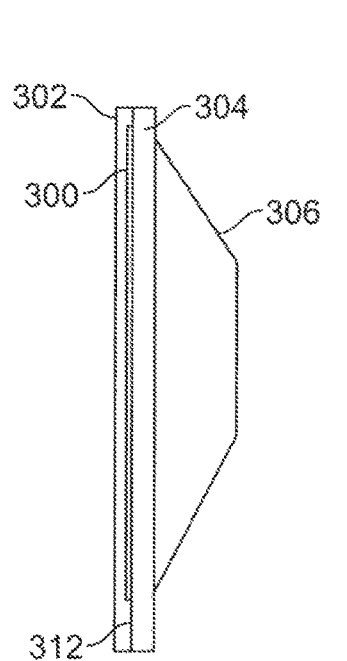
FIG. 6 is a diagrammatic representation of a side view of a tray table in a secured upright position, according to an embodiment of the present disclosure.

FIG. 5 is a diagrammatic representation of a front view of the tray table 300 in a secured upright position, according to an embodiment of the present disclosure. FIG. 6 is a diagrammatic representation of a side view of the tray table 300 in the secured upright position. In the secured upright position, an interior surface of the covering filter 302 abuts against an outer edge 312 of the reflective rim 304. For the sake of clarity, the reflective rim 304 is shown in FIG. 5, although it is to be understood that the covering filter 302 covers most, if not all, of the reflective rim 304 when viewed from the orientation shown in FIG. 5. The covering filter 302 may securely press against the reflective rim 304 to prevent unfiltered light from passing therebetween. As noted above, during operation of the sanitation assembly, the covering filter 302 filters the emitted UV light so that UV radiation is prevented from passing through the covering filter, but may allow certain wavelengths of light that are safe for viewing to pass therethrough in order to indicate that the sanitation assembly is operating.

The covering filter 302 may underlay an entirety of the tray table 300. Optionally, the covering filter 302 may provide a frame member that couples to outer edges of the tray table 300.

Figure 7:
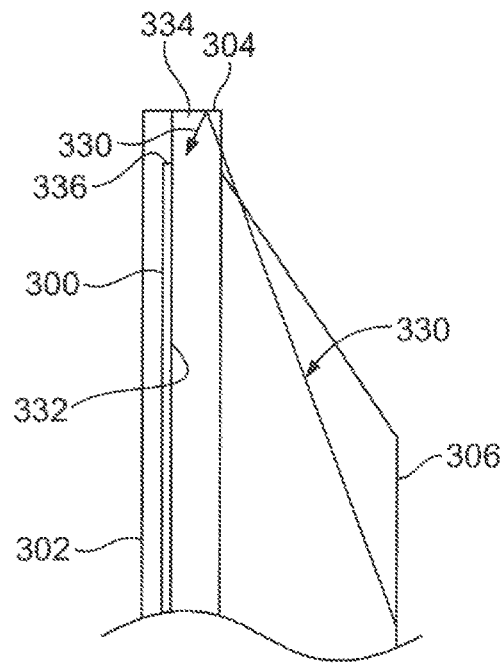
FIG. 7 is a diagrammatic representation of a side internal view of a sanitation assembly reflecting UV light onto a tray table, according to an embodiment of the present disclosure.

FIG. 7 is a diagrammatic representation of a side internal view of the sanitation assembly 306 reflecting UV light 330 onto the tray table 300, according to an embodiment of the present disclosure. The tray table 300 is shown in the secured, stowed, upright position in FIG. 7. The UV light source of the sanitation assembly 306 is not shown. The reflective surfaces of the sanitation assembly 306 are configured to reflect the UV light 330 onto most if, if not all, of a supporting surface 332 of the tray table 300. As shown, the UV light 330 may be emitted from the UV light source and reflected by reflective surfaces onto interior surfaces 334 of the reflective rim 304. The UV light 330 reflects off the interior surfaces 334 onto the supporting surface 332, including outer edge portions 336.

Figure 8:
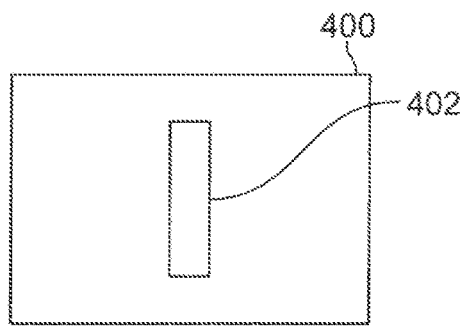
FIG. 8 is a diagrammatic representation of a front view of a sanitation assembly when a tray table is in a supporting position, according to an embodiment of the present disclosure.

FIG. 8 is a diagrammatic representation of a front view of a sanitation assembly 400 when a tray table (not shown in FIG. 8) is in a supporting position, according to an embodiment of the present disclosure. A shutter 402 may cover the UV light source 112 when the tray table is in the supporting position. The shutter 402 may be operatively coupled to a sanitation control unit, such as the sanitation control unit 114, which is shown and described with respect to FIG. 1. For example, the sanitation control unit 114 may move the shutter 402 to the closed position shown in FIG. 8 when the tray table is in the supporting position. In response to the tray table moving to the secured upright position, the sanitation control unit 114 may move the shutter 402 to an open position to expose the UV light source (see FIG. 9).

Optionally, the shutter 402 may be mechanically linked to the tray table so that movement of the tray table between the supporting position and the upright position moves the shutter 402 between corresponding positions (such as a closed position and an open position). For example, the shutter 402 may be mechanically linked to the tray table through one or more rods, gears, tracks, and/or the like. In such an embodiment, the shutter 402 need not be operatively coupled to the sanitation control unit 114. Instead, movement of the tray table between the supporting and upright positions automatically moves the shutter 402 in response thereto.

Figure 9:
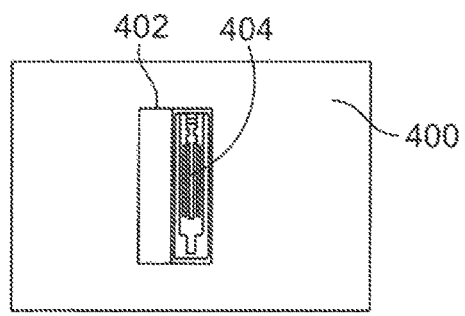
FIG. 9 is a diagrammatic representation of a front view of a sanitation assembly when a tray table is in a secured upright position, according to an embodiment of the present disclosure.

FIG. 9 is a diagrammatic representation of a front view of the sanitation assembly 400 when the tray table (not shown in FIG. 9) is in a secured upright position, according to an embodiment of the present disclosure. As shown, in the upright position, the shutter 402 is moved to expose the UV light source 404.

The shutter 402 shown and described with respect to FIGS. 8 and 9 may be used with any of the embodiments of the present disclosure. For example, the shutter 402 may be used with the sanitation assemblies shown and described with respect to FIGS. 1-7.

Figure 10:
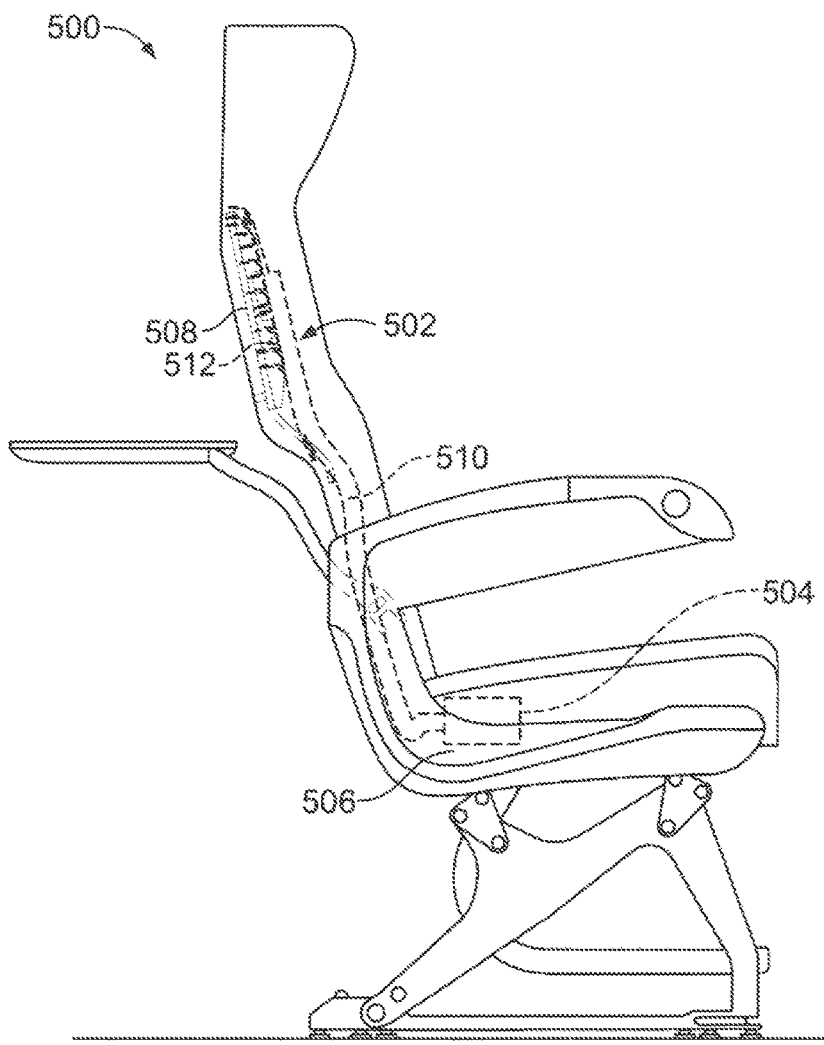
FIG. 10 is a diagrammatic representation of a side view of a seat assembly, according to an embodiment of the present disclosure.

FIG. 10 is a diagrammatic representation of a side view of a seat assembly 500, according to an embodiment of the present disclosure. The seat assembly 500 is similar to those described above, except that a sanitation assembly 502 may include a UV light source 504 secured within a portion of the seat assembly 500 (such as within seat cushion 506). The UV light source 504 may connect to a UV light emission surface 508 through a fiber optic cable 510. The fiber optic cable 510 may, in turn, connect to the UV light emission surface 508 through a plurality of fiber optic output ends or couplings 512.

Figure 11:
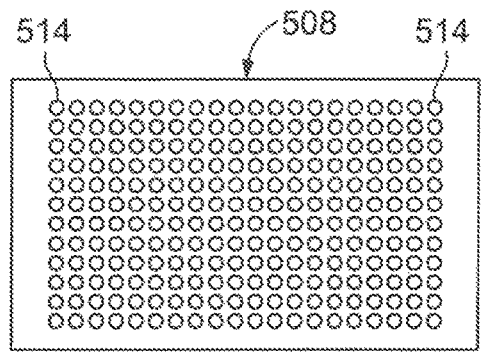
FIG. 11 is a diagrammatic representation of a front view of a UV light emission surface, according to an embodiment of the present disclosure.

FIG. 11 is a diagrammatic representation of a front view of the UV light emission surface 508 according to an embodiment of the present disclosure. The UV light emission surface 508 includes a plurality of light-emitting output ports 514 that are coupled to respective fiber optic couplings 512. The light-emitting output ports 514 may be sized, shaped, and spaced to emit light over an entire supporting surface of a tray table when the tray table is in a secured upright position.

Alternatively, instead of fiber optics, each of the light-emitting output ports 514 may be separate and distinct LEDs. In at least one embodiment, the LEDs may be positioned inside of the light-emitting output ports 514. Each LED may be configured to emit UV light. The LEDs may be operatively connected to a sanitation control unit, as described above. In such an embodiment, a separate UV light source within the seat assembly may not be needed.

Figure 12:
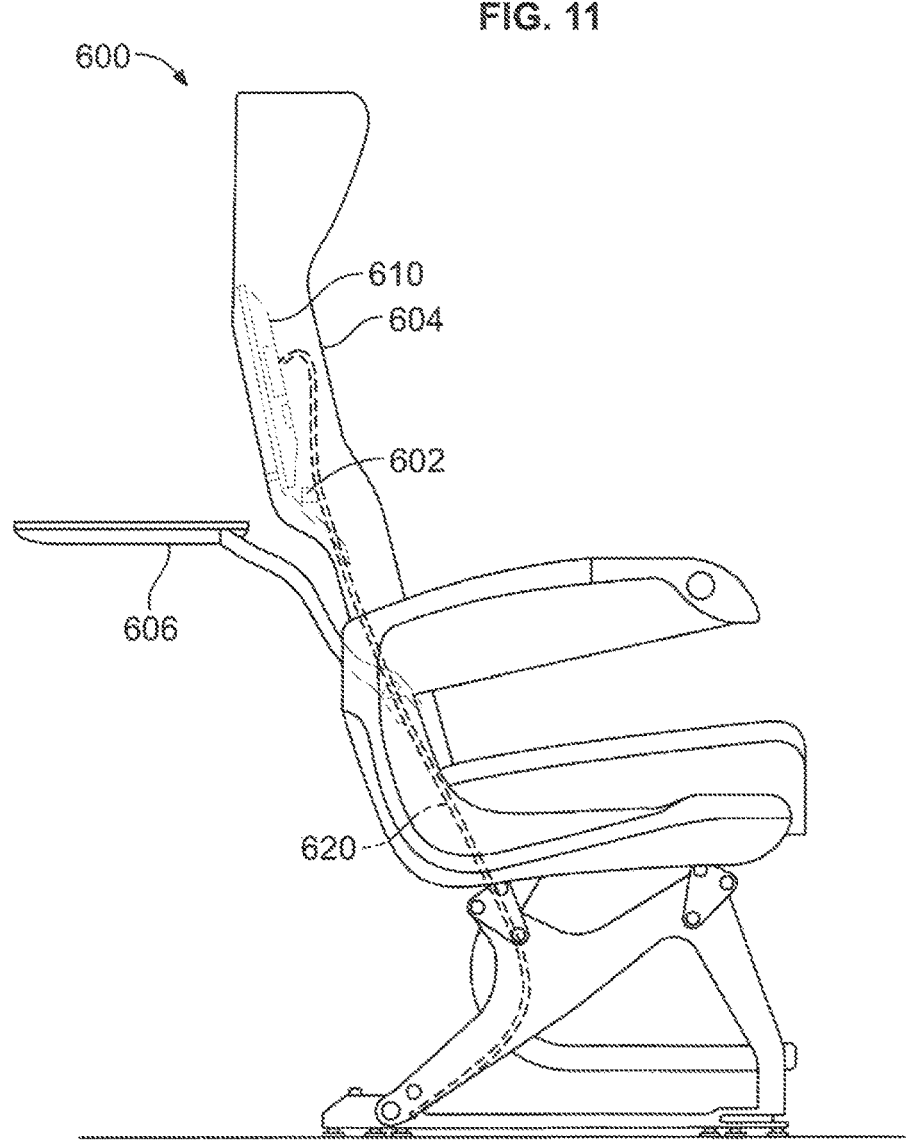
FIG. 12 is a diagrammatic representation of a side view of a seat assembly, according to an embodiment of the present disclosure.

FIG. 12 is a diagrammatic representation of a side view of a seat assembly 600, according to an embodiment of the present disclosure. The seat assembly 600 is similar to any of those described above. A tray table position sensor 602 may be secured within a portion of the seat assembly 600, such as a backrest 604. The tray table position sensor 602 may be any type of device configured to detect a position of a tray table 606. For example, the tray table position sensor 602 may be a Hall effect sensor in communication with a sanitation control unit. When the tray table is in a supporting position, the Hall effect sensor generates a first output, which is received by the sanitation control unit. The first output is correlated with a supporting position. When the tray table is in a secured upright position, the Hall effect sensor generates a second output, which is indicative of the changed position at the upright position.

As shown, the tray table position sensor 602 may be positioned in the backrest 604 towards a bottom edge of the tray table 606. Optionally, the tray table position sensor 602 may be positioned at various other portions of the seat assembly 600. For example, the tray table position sensor 602 may be positioned above the sanitation assembly 610, which may be a more reliable position for detecting the secured upright position. Further, additional tray table position sensors 602 may be used. Also, instead of a Hall effect sensor, the tray table position sensor 602 may be a light-emitting device, such as an infrared or laser, or various other position sensing devices.

A power cable 620 may connect the sanitation assembly 610 and/or the tray table position sensor 602 to a source of power, such as that within a vehicle. The power cable 620 may be secured within and extend through portions of the seat assembly 600. The power cable 620 may be used with any of the embodiments of the present disclosure.

Figure 13:
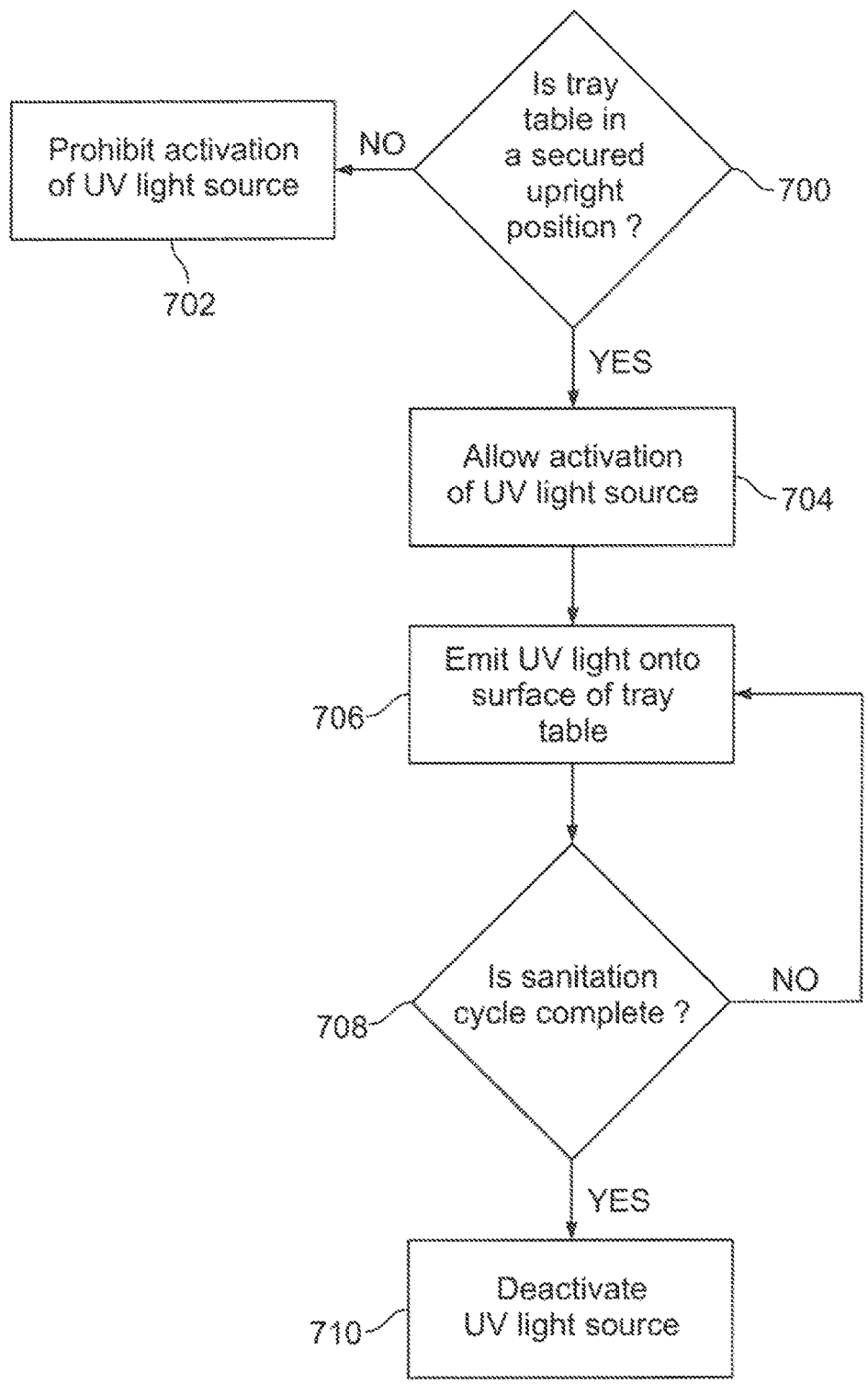
FIG. 13 illustrates a flow chart of a method of sanitizing a tray table secured to a seat assembly, according to an embodiment of the present disclosure.

FIG. 13 illustrates a flow chart of a method of sanitizing a tray table secured to a seat assembly, according to an embodiment of the present disclosure. At 700, it is determined if the tray table is in a secured upright position. If not, the method continues to 702, in which activation of a sanitation assembly is prohibited. For example, a sanitation control unit may detect whether the tray table is in the secured upright position. If the tray table is not in the secured upright position, the sanitation control unit prohibits activation of the UV light source.

If, however, the tray table is in the secured upright position, the method proceeds from 700 to 704, in which activation of the UV light source is allowed. In at least one embodiment, in response to the tray table transitioning to the secured upright position, the sanitation control assembly automatically initiates a sanitation cycle. In at least one other embodiment, the UV light source is allowed to be activated, and activated when a passenger engages an interface (such as an activation button, touch screen or the like), or vehicle crew personnel engages an interface (such as that of a master control unit). Once activated, UV light is emitted onto a surface of the tray table at 706. At 708, it is determined if a sanitation cycle is complete after activation of the UV light source. If not, the method returns to 706. If, however, the sanitation cycle is complete, the method proceeds to 710, in which the UV light source is deactivated.

In at least one embodiment, the UV light source may be automatically deactivated if the tray table moves out of a secured upright position. Notably, some tray tables may include a rotatable latch. In connection with such trays, the position of the latch may be sensed. Rotation of the latch out of a locked position may automatically deactivate the UV light source.

Figure 14:
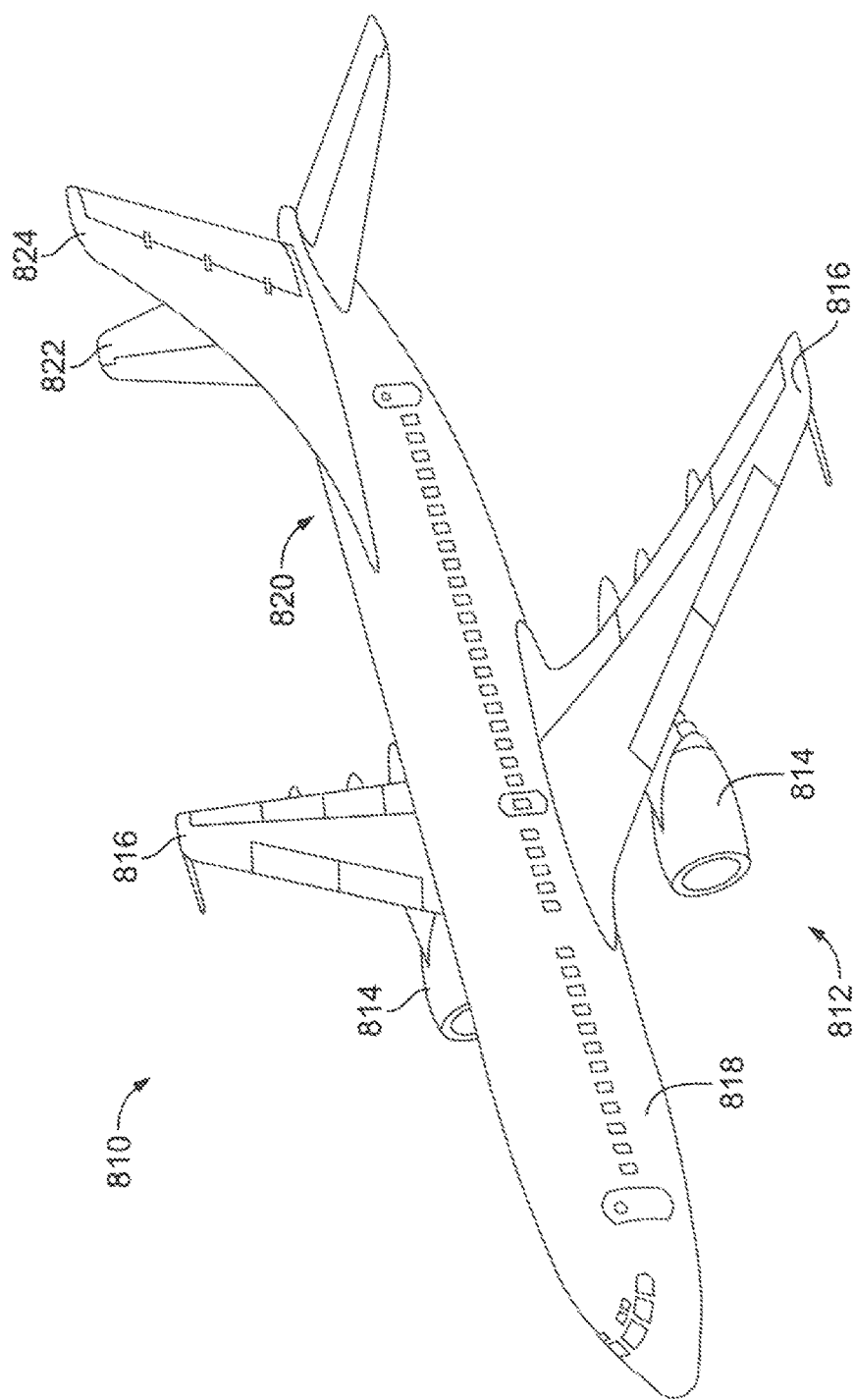
FIG. 14 is a diagrammatic representation of a perspective top view of an aircraft (or aircraft assembly), according to an embodiment of the present disclosure.

FIG. 14 is a diagrammatic representation of a perspective top view of an aircraft 810 (or aircraft assembly), according to an embodiment of the present disclosure. The aircraft 810 is an example of a vehicle having an interior space or cabin in which any of the systems and methods described above with respect to FIGS. 1-13 may be used. Alternatively, instead of an aircraft, the systems and methods of embodiments of the present disclosure may be used with various other vehicles, such as automobiles, buses, locomotives and train cars, seacraft, spacecraft, and the like.

The aircraft 810 may include a propulsion system 812 that may include two turbofan engines 814, for example. Optionally, the propulsion system 812 may include more engines 814 than shown. The engines 814 are carried by wings 816 of the aircraft 810. In other embodiments, the engines 814 may be carried by a fuselage 818 and/or an empennage 820. The empennage 820 may also support horizontal stabilizers 822 and a vertical stabilizer 824.

The fuselage 818 of the aircraft 810 defines an internal cabin, which may include a cockpit, one or more work sections (for example, galleys, personnel carry-on baggage areas, and the like), and one or more passenger sections (for example, first class, business class, and coach sections). Each of the sections may be separated by a cabin transition area, which may include a curtain assembly having a moveable curtain that may be selectively opened and closed within an aisle.

Figure 15:
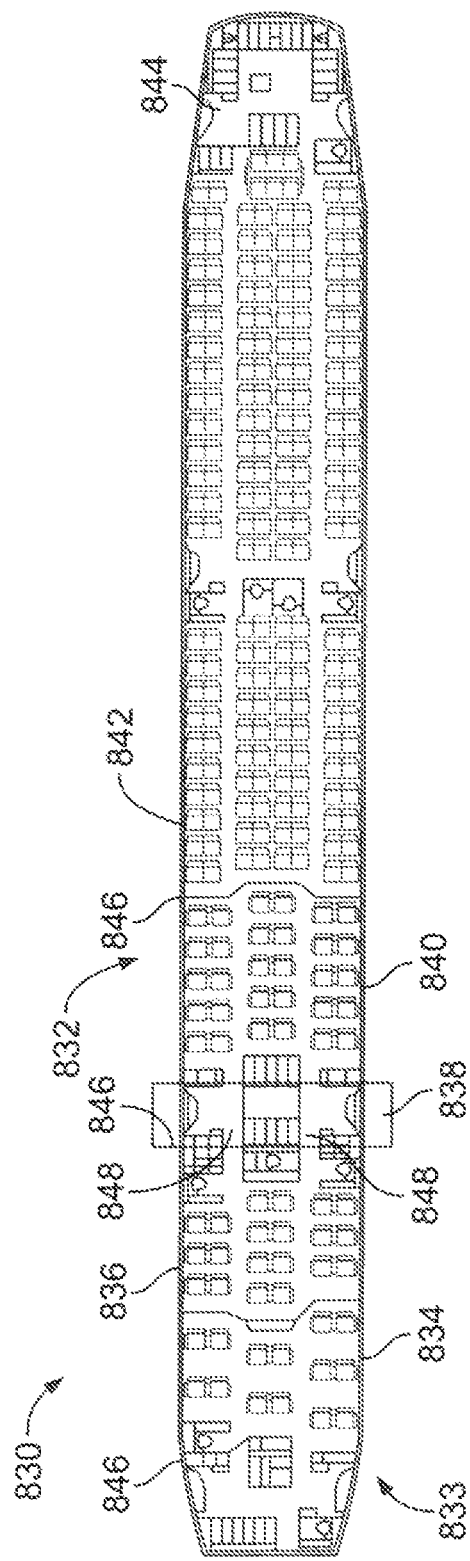
FIG. 15 is a diagrammatic representation of a top plan view of an internal cabin of an aircraft, according to an embodiment of the present disclosure.

FIG. 15 is a diagrammatic representation of a top plan view of an internal cabin 830 of an aircraft, according to an embodiment of the present disclosure. The internal cabin 830 may be within a fuselage 832 of the aircraft. The internal cabin 830 may include multiple sections, including a front light ring section 833, a first class section 834, a business class section 836, a front galley section 838, an expanded economy or coach section 840, a standard economy of coach section 842, and a rear galley section 844. It is to be understood that the internal cabin 830 may include more or less sections than shown. For example, the internal cabin 830 may not include a first class section, and may include more or less galley sections than shown. Each of the sections may be separated by a cabin transition area 846, which may include curtain assemblies between structural features (such as monuments, overhead bins, or the like) within aisles 848.

Figure 16:
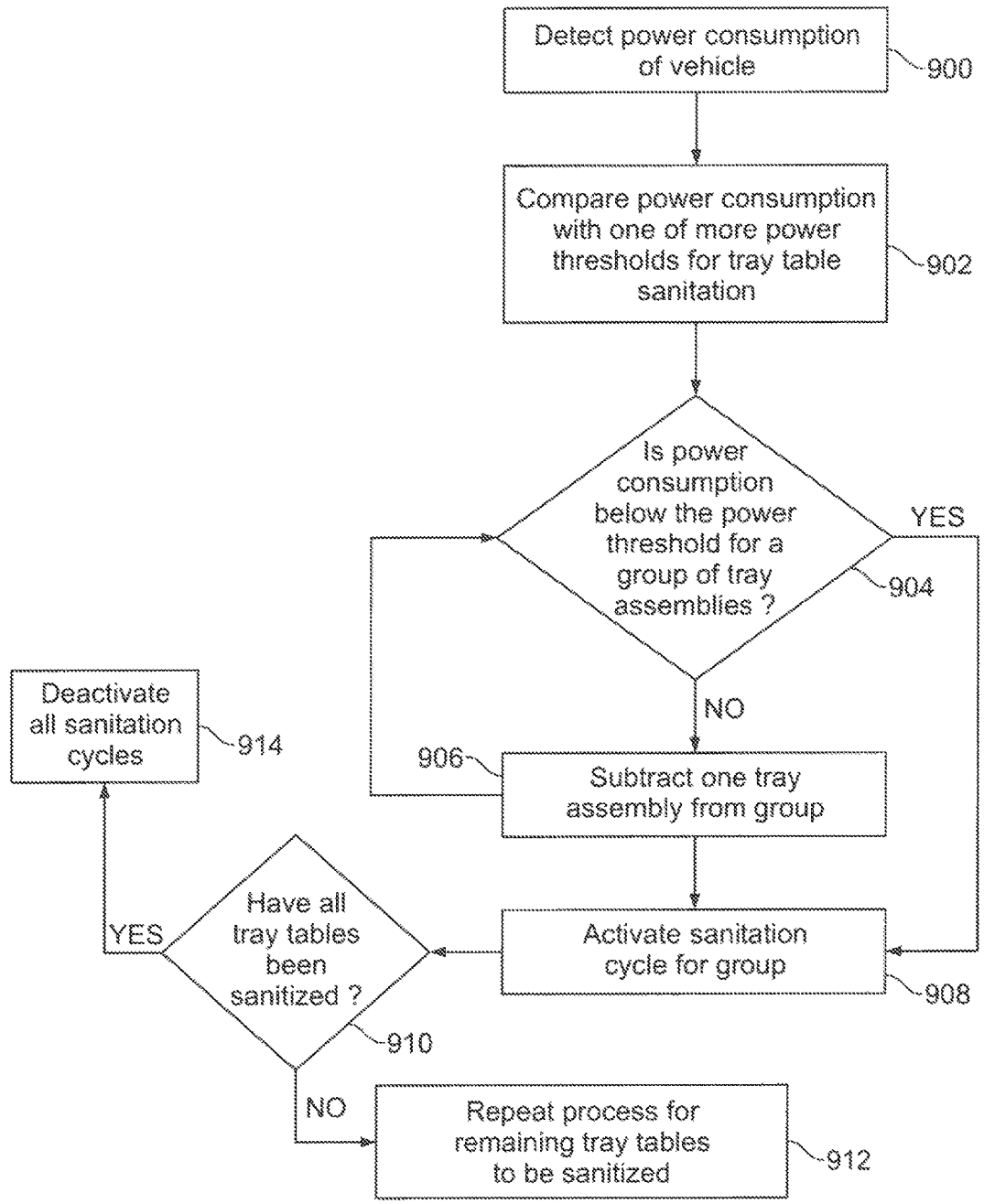
FIG. 16 illustrates a flow chart of a method of sanitizing multiple tray tables within a vehicle, according to an embodiment of the present disclosure.

FIG. 16 illustrates a flow chart of a method of sanitizing multiple tray tables within a vehicle, according to an embodiment of the present disclosure. The method begins at 900, in which a power consumption of a vehicle is detected. For example, a master control unit may detect an overall power consumption of the vehicle.

At 902, the detected power consumption is compared with one or more power thresholds for tray table sanitation. For example, the master control unit may store the power threshold(s). A first power threshold may be in relation to one tray table. A second power threshold may be in relation to multiple tray tables, such as groups of tray tables (for example, tray tables within one or more rows, sections, or the like within the vehicle).

At 904, it is determined (such as by the master control unit) if the detected power consumption is below the power threshold for a group of tray assemblies. If not, one tray assembly may be subtracted from the group (such as the master control circuit subtracting a tray assembly) at 906. The method then returns to 904.

If, however, the detected power consumption is below the power threshold, the method proceeds from 904 to 908, in which a sanitation cycle is activated from the group of tray tables. The sanitation cycle may last as long as dictated by data stored in memory of the master control unit, for example, and/or within sanitation control units of each sanitation assembly operatively connected to the tray tables.

Once the sanitation cycle is completed, it is determined if all of the tray tables have been sanitized at 910. If not, the method continues to 912, in which the process is repeated for the tray tables to be sanitized. If, however, all of the tray tables have been sanitized, the method proceeds from 910 to 914, in which all sanitation cycles for all of the tray tables are deactivated.

Referring to FIGS. 1-16, embodiments of the present disclosure provide efficient and effective systems and methods of sanitizing one or more tray tables, such as may be found in a vehicle. Passengers may be able to activate sanitation cycles when tray tables are secured in stowed, upright positions. Optionally, one or more crew members of a vehicle, such as flight attendants, may activate a sanitation cycle for multiple stowed tray tables.

In at least one other embodiment, a sanitation assembly may include a UV light source that may be activated when the tray table is not in the secured upright position, such as when the tray table is in a supporting position. In such an embodiment, the UV light source may include an output that is moveable and able to be focused or emitted onto various surfaces in proximity to a seat assembly. In at least one embodiment, the UV light source may focus on supporting surfaces of seat cushions to sanitize the seat cushions. Flight attendants may control movement of the UV light source through the master control unit, a passenger interface, or through manual manipulation. For example, operation of the UV light source when the tray table is not secured in the upright position (such as to sanitize a seat cushion sanitation) may be an option only for flight crew, and may be used when no passengers are in the cabin.

As used herein, the term "central processing unit," "CPU," "computer," "control unit," "module," or the like may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "central processing unit," "CPU," "computer," "control unit," or "module."

The computer or processor executes a set of instructions that are stored in one or more storage elements (such as one or more memories), in order to process data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The diagrams of embodiments herein may illustrate one or more control units or modules. It is to be understood that the control units or modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the modules may represent processing circuitry such as one or more of a field programmable gate array (FPGA), application specific integrated circuit (ASIC), microprocessor(s), a quantum computing device, and/or the like. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method of sanitizing a tray table, the method comprising:
    detecting when the tray table is secured in an upright position with a tray table position sensor;
    emitting ultraviolet (UV) light from a UV light source onto the tray table when the tray table is secured in the upright position; and
    preventing emission of the UV light from the UV light source when the tray table is not secured in the upright position.

2. The method of claim 1, further comprising securing the UV light and the tray table to one or more portions of a seat assembly.

3. The method of claim 1, wherein the emitting comprises emitting UV germicidal irradiation from one or more of a low pressure mercury discharge lamp, one or more fiber optic couplings, or one or more light emitting diodes.

4. The method of claim 1, further comprising using a passenger interface to allow a passenger to activate a sanitation cycle when the tray table is secured in the upright position.

5. The method of claim 1, further comprising using a master control unit remotely located from the tray table to control the emitting and preventing operations.

6. The method of claim 1, wherein the emitting operation comprises reflecting the UV light by one or more reflective surfaces of the tray table onto surfaces of the tray table.

7. The method of claim 1, further comprising using a covering filter to filter the UV light proximate to edge portions of the tray table during the emitting operation.

8. The method of claim 1, further comprising:
    moving a shutter to a closed position that covers the UV light source when the tray table is not secured in the upright position, and
    moving the shutter to an open position that exposes the UV light source when the tray table is secured in the upright position.

9. A method of sanitizing a tray table, the method comprising:
    emitting ultraviolet (UV) light from a UV light source onto the tray table when the tray table is secured in an upright position, wherein the emitting operation comprises reflecting the UV light by one or more reflective surfaces of the tray table onto surfaces of the tray table.

10. The method of claim 9, further comprising detecting when the tray table is secured in the upright position with a tray table position sensor.

11. The method of claim 9, further comprising securing the UV light and the tray table to one or more portions of a seat assembly.

12. The method of claim 9, further comprising using a passenger interface to allow a passenger to activate a sanitation cycle when the tray table is secured in the upright position.

13. The method of claim 9, further comprising using a master control unit remotely located from the tray table to control the emitting and preventing operations.

14. The method of claim 9, further comprising using a covering filter to filter the UV light proximate to edge portions of the tray table during the emitting operation.

15. The method of claim 9, further comprising:
   moving a shutter to a closed position that covers the UV light source when the tray table is not secured in the upright position, and
   moving the shutter to an open position that exposes the UV light source when the tray table is secured in the upright position.

16. A method of sanitizing a tray table, the method comprising:
   detecting when the tray table is secured in an upright position with a tray table position sensor; and
   emitting ultraviolet (UV) light from a UV light source onto the tray table when the tray table is secured in the upright position.

17. The method of claim 16, further comprising securing the UV light and the tray table to one or more portions of a seat assembly.

18. The method of claim 16, further comprising using a master control unit remotely located from the tray table to control the emitting and preventing operations.

19. A method of sanitizing a tray table, the method comprising:
   emitting ultraviolet (UV) light from a UV light source onto the tray table when the tray table is secured in an upright position, wherein the emitting operation comprises reflecting the UV light by one or more reflective surfaces of the tray table onto surfaces of the tray table; and
   preventing emission of the UV light from the UV light source when the tray table is not secured in the upright position.

20. The method of claim 19, further comprising securing the UV light and the tray table to one or more portions of a seat assembly.

21. The method of claim 19, wherein the emitting comprises emitting UV germicidal irradiation from one or more of a low pressure mercury discharge lamp, one or more fiber optic couplings, or one or more light emitting diodes.

22. The method of claim 19, further comprising using a passenger interface to allow a passenger to activate a sanitation cycle when the tray table is secured in the upright position.

23. The method of claim 19, further comprising using a master control unit remotely located from the tray table to control the emitting and preventing operations.

24. The method of claim 19, further comprising using a covering filter to filter the UV light proximate to edge portions of the tray table during the emitting operation.

25. The method of claim 19, further comprising:
   moving a shutter to a closed position that covers the UV light source when the tray table is not secured in the upright position, and
   moving the shutter to an open position that exposes the UV light source when the tray table is secured in the upright position.

* * * * *